(12) United States Patent
Pianca et al.

(10) Patent No.: US 8,805,544 B2
(45) Date of Patent: *Aug. 12, 2014

(54) INSERTION TOOL FOR PADDLE-STYLE ELECTRODE

(71) Applicant: Boston Scientific Neuromodulation Corporation, Valencia, CA (US)

(72) Inventors: Anne Margaret Pianca, Santa Monica, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/189,235

(22) Filed: Feb. 25, 2014

(65) Prior Publication Data

US 2014/0180305 A1 Jun. 26, 2014

Related U.S. Application Data

(60) Division of application No. 13/523,562, filed on Jun. 14, 2012, now Pat. No. 8,706,259, which is a continuation-in-part of application No. 11/117,814, filed on Apr. 29, 2005, now Pat. No. 8,224,459.

(60) Provisional application No. 60/566,959, filed on Apr. 30, 2004.

(51) Int. Cl.
*A61N 1/05* (2006.01)

(52) U.S. Cl.
CPC ................................ *A61N 1/0553* (2013.01)
USPC ........................................................ 607/117

(58) Field of Classification Search
USPC ........................................................ 607/117
See application file for complete search history.

(56) References Cited

U.S. PATENT DOCUMENTS

| 3,646,940 A | 3/1972 | Timm et al. |
| 3,724,467 A | 4/1973 | Avery et al. |

(Continued)

FOREIGN PATENT DOCUMENTS

EP 1048270 A1 11/2000

OTHER PUBLICATIONS

Advisory Action mailed Mar. 13, 2008 for U.S. Appl. No. 11/117,814.

(Continued)

*Primary Examiner* — Eric D. Bertram
(74) *Attorney, Agent, or Firm* — Lowe Graham Jones PLLC; Bruce E. Black (57) ABSTRACT

A system for lead implantation includes a lead having a paddle-style electrode extending from a proximal end to a distal end, the paddle-style electrode, having a back surface; an active surface; a plurality of electrode contacts disposed on the active surface; and a longitudinal lumen extending into the paddle-style electrode and defining an opening at the proximal end of the paddle-style electrode. The lead also has at least one lead body extending from the paddle-style electrode. The at least one lead body includes conductors that are electrically coupled to the electrode contracts. The system also includes an insertion tool having a distal portion for insertion into the longitudinal lumen of the paddle-style electrode. At least the distal portion of the insertion tool or the longitudinal lumen (or both) includes a low friction material forming a surface with a coefficient of friction of 0.1 or less.

20 Claims, 10 Drawing Sheets

(56) References Cited

U.S. PATENT DOCUMENTS

| | | | |
|---|---|---|---|
| 4,141,365 A | 2/1979 | Fischell et al. | |
| 4,166,469 A | 9/1979 | Littleford | |
| 4,270,549 A | 6/1981 | Heilman | |
| 4,291,707 A | 9/1981 | Heilman et al. | |
| 4,379,462 A | 4/1983 | Borkan et al. | |
| 4,512,351 A | 4/1985 | Pohndorf | |
| 4,765,341 A | 8/1988 | Mower et al. | |
| 4,989,617 A | 2/1991 | Memberg et al. | |
| 5,143,067 A | 9/1992 | Rise et al. | |
| 5,249,574 A | 10/1993 | Bush et al. | |
| 5,282,468 A | 2/1994 | Klepinski | |
| 5,391,200 A | 2/1995 | KenKnight et al. | |
| 5,397,342 A | 3/1995 | Heil, Jr. et al. | |
| 5,417,719 A | 5/1995 | Hull et al. | |
| 5,618,287 A | 4/1997 | Fogarty et al. | |
| 5,643,330 A | 7/1997 | Holsheimer et al. | |
| 5,733,322 A | 3/1998 | Starkebaum | |
| 6,027,456 A | 2/2000 | Feler et al. | |
| 6,205,361 B1 | 3/2001 | Kuzma et al. | |
| 6,249,707 B1 * | 6/2001 | Kohnen et al. | 607/117 |
| 6,309,401 B1 | 10/2001 | Redko et al. | |
| 6,319,241 B1 | 11/2001 | King et al. | |
| 6,415,187 B1 | 7/2002 | Kuzma et al. | |
| 6,516,227 B1 | 2/2003 | Meadows et al. | |
| 6,522,932 B1 | 2/2003 | Kuzma et al. | |
| 6,553,264 B2 | 4/2003 | Redko et al. | |
| 6,605,094 B1 | 8/2003 | Mann et al. | |
| 6,714,822 B2 | 3/2004 | King et al. | |
| 6,895,283 B2 | 5/2005 | Erickson et al. | |
| 8,224,459 B1 | 7/2012 | Pianca et al. | |
| 2010/0179562 A1 * | 7/2010 | Linker et al. | 606/129 |
| 2012/0271315 A1 | 10/2012 | Pianca et al. | |
| 2012/0271316 A1 | 10/2012 | Pianca et al. | |
| 2013/0066331 A1 * | 3/2013 | Chitre et al. | 606/129 |
| 2013/0268041 A1 | 10/2013 | Schulte et al. | |

OTHER PUBLICATIONS

Appeal Brief mailed Jun. 20, 2008 for U.S. Appl. No. 11/117,814.
Examiner's Answer mailed Sep. 3, 2008 for U.S. Appl. No. 11/117,814.
Final Rejection mailed Jan. 22, 2008 for U.S. Appl. No. 11/117,814.
Final Rejection mailed Nov. 29, 2013 for U.S. Appl. No. 13/523,562.
Final Rejection mailed Jun. 4, 2013 for U.S. Appl. No. 13/536,561.
Final Rejection mailed Jul. 15, 2011 for U.S. Appl. No. 11/117,814.
Final Rejection mailed Sep. 23, 2011 for U.S. Appl. No. 11/117,814.
Non-Final Office Action mailed Feb. 13, 2013 for U.S. Appl. No. 13/536,561.
Non-Final Office Action mailed Feb. 18, 2011 for U.S. Appl. No. 11/117,814.
Non-Final Office Action mailed Jul. 10, 2013 for U.S. Appl. No. 13/523,562.
Non-Final Office Action mailed Aug. 7, 2007 for U.S. Appl. No. 11/117,814.
Reply Brief mailed Nov. 3, 2008 for U.S. Appl. No. 11/117,814.
Suppelmental Non-Final Office Action mailed Feb. 28, 2011 for U.S. Appl. No. 11/117,814.
U.S. Appl. No. 13/536,561 Official Communication dated Jun. 4, 2013.
U.S. Appl. No. 13/536,561, Official Communication mailed Feb. 13, 2013.
Official Communication for U.S. Appl. No. 14/100,292 mailed Mar. 20, 2014.

* cited by examiner

INSERTION TOOL FOR PADDLE-STYLE ELECTRODE

The present application is a divisional application of U.S. patent application Ser. No. 13/523,562 filed Jun. 14, 2012, now U.S. Pat. No. 8,706,259, which is a continuation-in-part of U.S. patent application Ser. No. 11/117,814, filed Apr. 29, 2005, now U.S. Pat. No. 8,224,459, which claims the benefit of U.S. Provisional Patent Application Ser. No. 60/566,959, filed Apr. 30, 2004, all of which are incorporated herein by reference.

FIELD OF THE INVENTION

The present disclosure relates to electrical stimulation systems and methods and, more particularly, relates to insertion and/or implantation steering tools and methods used with implantable paddle-style electrodes, e.g., used for stimulating nerve or muscle, for example, the spinal column to relieve chronic pain.

BACKGROUND OF THE INVENTION

The term "electrode contact" will be used herein to describe a conductive element in the lead. The term "lead" will be used herein to describe the device that may be connected to an implantable stimulator for carrying stimulation current from the stimulator to the electrode contact on the lead. The term "electrode" will be used to describe that portion (usually the distal end) of the lead that includes the electrode contact(s). The term "electrode array" will refer to that portion of the lead having a multiplicity of electrode contacts.

Spinal cord stimulation is a well accepted clinical method for reducing pain in certain populations of patients. An SCS system typically includes an Implantable Pulse Generator (IPG), an electrode, electrode lead, and an electrode lead extension. The electrode is implanted along the dura of the spinal cord, and the IPG generates electrical pulses that are delivered, through the electrode contacts, to the dorsal column and dorsal root fibers within the spinal cord. Individual electrode contacts are arranged in a desired pattern and spacing in order to create an electrode array. Individual wires within the electrode lead connect with each electrode contact in the array. The electrode lead exits the spinal column and generally attach to an electrode lead extension. The electrode lead extension, in turn, is typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of the Spinal Cord," teaches an electrode implant for the neuro-stimulation of the spinal cord. A relatively thin and flexible strip of physiologically inert plastic is provided on which a plurality of electrode contacts are formed. The electrode contacts are connected electrically to an RF receiver, which is also implanted.

Most of the electrode arrays used with known SCS systems employ between 4 and 16 electrodes. Electrodes are selectively programmed to act as anodes, cathodes, or left off, creating a stimulating group. The number of stimulation groups available, combined with the ability of integrated circuits to generate a variety of complex stimulation pulses, presents a huge selection of stimulation parameter sets to the clinician. When an SCS system is implanted, a "fitting" procedure is performed to select an effective stimulation parameter set for a particular patient.

In order to achieve an effective result from spinal cord stimulation, the lead or leads should be placed in a location such that the electrical stimulation will affect the targeted nerves and cause paresthesia. The paresthesia perceived by the patient and induced by the stimulation masks the pain that is the target of treatment. If a lead is not correctly positioned, it is possible that the patient will receive little or no benefit from an implanted SCS system. Thus, correct lead placement can mean the difference between effective and ineffective pain therapy. During surgery, the physician places the leads in a very careful manner in order to locate the electrode contacts proximal to neural elements that are the target of the stimulation. During and after placement, stimulation energy is delivered to verify that the leads are indeed stimulating the appropriate neural elements.

If the lead(s) happen to shift position after implant, the targeted neural fibers may no longer be appropriately stimulated. At best, this can require electrical reprogramming to restore therapy or, at worst, surgical revision, where a second surgery is required and the leads must be manually readjusted. In the first case, the physician may have only a suspicion that a lead has shifted position, based on patient reporting of paresthesia, which is not foolproof. Also, attempting to reprogram the leads based on paresthesia locations can be challenging.

There are two major types of electrodes used for spinal cord stimulation: (1) percutaneously implanted in-line electrodes, requiring local anesthesia for implant, and (2) paddle-shaped electrodes, requiring major surgery for implantation.

The first type of electrode, i.e., the in-line electrode, comprises thin, cylindrical-style electrodes. Such in-line or cylindrical-style electrodes are easier and less invasive to implant, typically requiring only local anesthesia and the use of a large gauge needle, for example a 15 gauge Touhy needle. Disadvantageously, such in-line electrodes are not as stable as a paddle-shaped electrodes, as they may be more easily pulled out or pushed into the tissue and are therefore prone to migration.

The second type of electrode, i.e., the paddle-shaped electrode, provides a large-area electrode surface to contact the body tissue. Advantageously, such paddle-style electrodes are more stable than in-line electrodes, after implant. Moreover, such paddle-style electrodes provide a platform for multiple sets of electrodes in many possible configurations to thereby optimize electrode programming and clinical results. In contrast, the percutaneous in-line electrodes can only combine electrodes in a vertical or linear row. Disadvantageously, however, the paddle style electrodes require complex major surgery and must be precisely maneuvered into place during implantation.

An insertion needle for introduction of a paddle-style electrode near the spinal column or other nervous system is described in U.S. Pat. Nos. 6,309,401, 6,553,264, and 6,249,707, all having the same assignee and all incorporated herein by reference.

U.S. Pat. No. 6,319,241, incorporated herein by reference, discloses techniques for implanting a lead having therapy delivery elements, such as electrodes or drug delivery ports, within a vertebral or cranial bone so as to maintain these elements in a fixed position relative to a desired treatment site. The described techniques in the '241 patent focus on the fixation method for the electrodes or drug delivery ports.

U.S. Pat. No. 6,027,456, incorporated herein by reference, describes an apparatus for assisting in the placement of the spinal cord stimulation lead with respect to the dorsal column of a patient. The invention described in the '456 patent focuses on detecting evoked potentials which result from the controlled stimulation of spinal nerves. An insertion tool used to assist in steering the lead in place is not described.

A need exists for an improved simple-to-use implant tool that affords steerability of a paddle-style electrode during insertion and implantation without the risk of damaging the insulation and/or conductors of the paddle-style electrode.

SUMMARY OF THE INVENTION

In view of the above, the present disclosure addresses the above and other needs by providing an insertion and implantation method, tool, and system to assist the surgeon in maneuvering or steering a paddle-style electrode in the localized area to be stimulated.

That is, in one aspect, the present disclosure provides various embodiments for the insertion tool that can be used to orient the paddle-style electrode during insertion and implantation without the attendant risk of damaging the electrode contacts.

In accordance with the present disclosure, the insertion or guiding tool used during implantation of a paddle-style electrode offers the benefit of reducing the risk of imparting any damage to the electrodes as compared to current techniques and devices used by medical professionals.

In accordance with the present disclosure, embodiments of the insertion tool present various means for engaging or holding the paddle-style electrode using a platform engager to thereby allow the surgeon to maneuver or steer the paddle-style electrode in both the medial/lateral and inferior/superior directions within the epidural space of the spinal column.

In accordance with yet another embodiment of the present disclosure, a stylet can be used as the platform engager to steer the paddle electrode in both the medial/lateral and inferior/superior directions within the epidural space of the spinal column, maintaining the electrode contacts facing downward during implantation. The stylet can be used alone or in conjunction with another configuration of the insertion tools described herein. The paddle-style electrode can be constructed having projections defining a stylet lumen to permit insertion of a steering stylet through the lumen.

In one embodiment, the insertion tool can be characterized as having a "pin fork" construction, where the fork end (two insertion pins) of the tool engage the paddle-style electrode, maintaining the electrode contacts facing downward during implantation. It is a feature of this embodiment of the paddle-style electrode to have access holes wherein the fork ends or pins of the insertion tool can be inserted. These holes may be located in the insulted area of the electrode, avoiding the area of the electrode contacts. The fork ends of the tool can either engage the paddle-style electrode from the active surface, back surface, or side edge surfaces, wherein the active surface is the electrode side and the back surface is parallel to the electrode side.

In another embodiment, the insertion tool can be characterized as having another platform engager having a "shovel" construction, wherein the end of the insertion tool contains a "shovel" like engaging configuration having a carrier. The paddle-style electrode is engaged by the carrier feature of the tool in the insulated area of the electrode avoiding the area where the electrode contacts are located. The carrier feature of the tool can either engage the paddle-style electrode from the active surface or back surface, wherein the active surface is the electrode side and the back surface is parallel to the electrode side and wherein the electrode platform fits within the carrier of the tool. A ridge or stopper can be added to the back surface of the paddle-style electrode to hold the tool in place, thereby allowing the surgeon the accessibility to maneuver or steer the paddle-style electrode in both the medial/lateral and inferior/superior directions within the epidural space of the spinal column, while maintaining the electrode contacts facing downward toward the stimulation site during implantation.

It is thus a feature of the present disclosure to provide several embodiments of a platform engager which is simple-to-use, allowing a medical professional the feasibility of steering a paddle-style electrode in the proximal location of the stimulation site above the dura of a patient's spinal cord. As part of the SCS system, the localized paddle-style electrode will thus deliver effective pain therapy.

Another embodiment is a system for lead implantation including a lead having a paddle-style electrode extending from a proximal end to a distal end, the paddle-style electrode, having a back surface; an active surface; a plurality of electrode contacts disposed on the active surface; and a longitudinal lumen extending into the paddle-style electrode and defining an opening at the proximal end of the paddle-style electrode. The lead also has at least one lead body extending from the paddle-style electrode. The at least one lead body includes a plurality of conductors that are electrically coupled to the plurality of electrode contacts. The system also includes an insertion tool having a distal portion configured and arranged for insertion of the distal portion of the insertion tool into the longitudinal lumen of the paddle-style electrode. At least the distal portion of the insertion tool includes a low friction material forming a surface of the distal portion of the insertion tool with a coefficient of friction of 0.1 or less.

Yet another embodiment is a system for lead implantation including a lead having a paddle-style electrode extending from a proximal end to a distal end, the paddle-style electrode, having a back surface; an active surface; a plurality of electrode contacts disposed on the active surface; and a longitudinal lumen extending into the paddle-style electrode and defining an opening at the proximal end of the paddle-style electrode. The lead also has at least one lead body extending from the paddle-style electrode. The at least one lead body includes a plurality of conductors that are electrically coupled to the plurality of electrode contacts. The system also includes an insertion tool having a distal portion configured and arranged for insertion of the distal portion of the insertion tool into the longitudinal lumen of the paddle-style electrode. The distal portion of the insertion tool is tapered to narrow a lateral width of the insertion tool along the distal portion.

A further embodiment is a lead including a paddle-style electrode extending from a proximal end to a distal end, the paddle-style electrode having a back surface; an active surface; a plurality of electrode contacts disposed on the active surface; and a longitudinal lumen extending into the paddle-style electrode and defining an opening at the proximal end of the paddle-style electrode. The longitudinal lumen is configured and arranged for receiving a distal portion of an insertion tool and the longitudinal lumen has an interior surface with a coating of low friction material disposed on the interior surface to provide the interior surface with a coefficient of friction of 0.1 or less. The lead also includes at least one lead body extending from the paddle-style electrode. The at least one lead body includes a plurality of conductors that are electrically coupled to the plurality of electrode contacts.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1A, 1B:
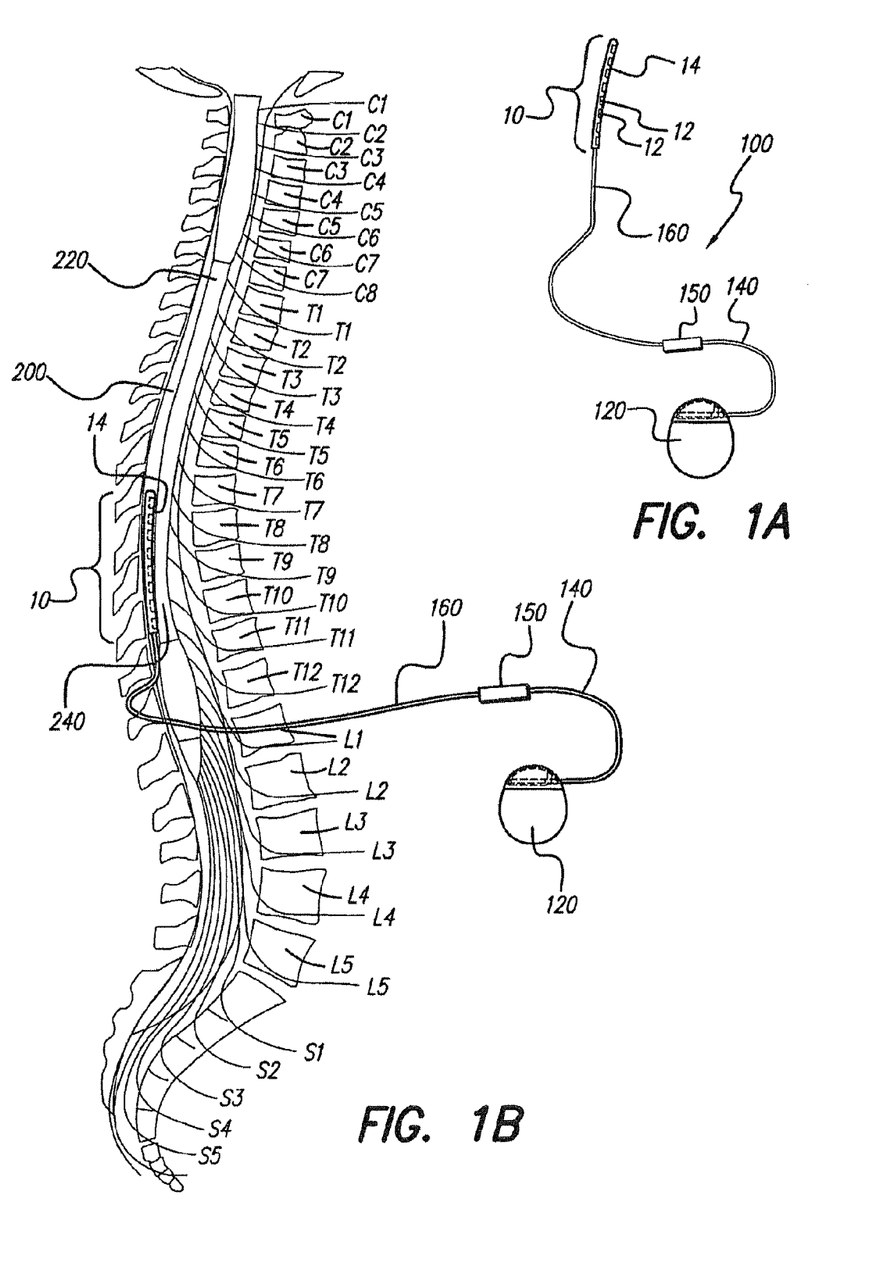
FIG. 1A shows a Spinal Cord Stimulation (SCS) system including therein a paddle-style electrode.
FIG. 1B depicts the SCS system of FIG. 1 implanted in a spinal column.

For illustration purposes, the following description of the present disclosure is shown in conjunction with a Spinal Cord Stimulation (SCS) system. A typical SCS system 100 is shown in FIG. 1A. The SCS system 100 typically comprises a rechargeable, multichannel, 16-contact (or more), telemetry-controlled pulse generator housed, for instance, in a rounded titanium hermetically sealed enclosure, known as an Implantable Pulse Generator (IPG) 120. The SCS system 100 may also contain a lead extension 140, an electrode lead 160, and an electrode array, wherein the electrode array depicted in FIG. 1A comprises a paddle-style electrode 10. The IPG 120 generates stimulation current for implanted electrode contacts that make up the paddle-style electrode 10. A proximal end of the lead extension 140 is removably connected to the IPG 120 and a distal end of the lead extension 140 is removably connected to a proximal end of the electrode lead 160 using connector 150, and electrode array 10 is formed on a distal end of the electrode lead 160. The in-series combination of the lead extension 140 and electrode lead 160, carry the stimulation current from the IPG 120 to the electrode array 10 to produce "paresthesia". Note, as used herein, the term "paresthesia" refers to that area or volume of the patient's tissue that is affected by the electrical stimuli applied through the electrode array. The patient may typically describe the paresthesia as an area where a tingling sensation is felt.

The SCS system 100 described in FIG. 1A above, is depicted implanted in the epidural space 200 in FIG. 16. The paddle-style electrode 10 is implanted at the site of nerves that are the target of stimulation, e.g., along the spinal cord 220 through an incision previously made during surgery. The paddle-style electrode 10 is orientated having the electrode surface or active surface 14 facing the stimulation site 240, wherein a plurality of electrode contacts 12 are arranged in a specified pattern along active surface 14. Due to the lack of space near the location where the electrode lead 160 exits the spinal column, the IPG 120 is generally implanted in the abdomen or above the buttocks. The lead extension 140 facilitates locating the IPG 120 away from the electrode lead exit point.

A more detailed description of a representative SCS system that may be used with the present disclosure is described in U.S. Pat. No. 6,516,227, issued Feb. 4, 2003, incorporated herein by reference. It is to be emphasized, however, that the invention herein described may be used with many different types of stimulation systems, and is not limited to use only with the representative SCS system described in the U.S. Pat. No. 6,516,227.

Figure 2A:
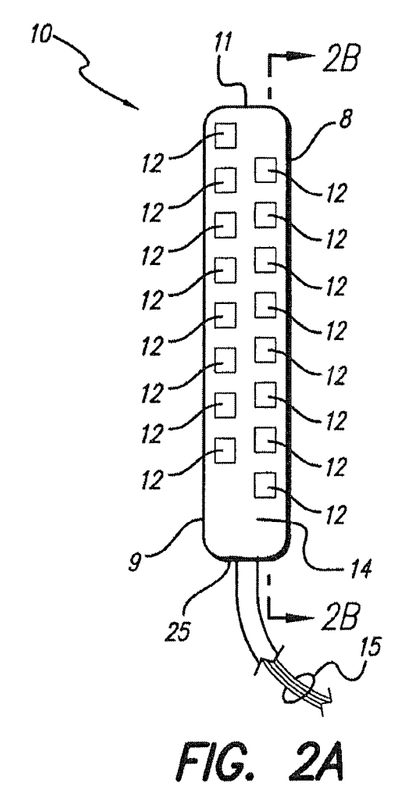
FIG. 2A is a planar view of a paddle-style electrode of the present disclosure.
Figure 2B:
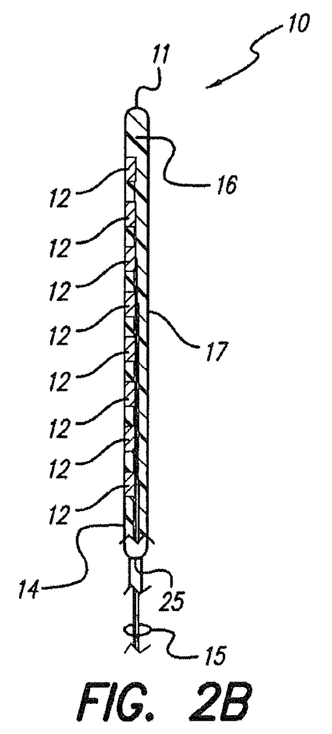
FIG. 2B is a sectional view of a paddle-style electrode of the present disclosure taken along line 2B-2B shown in FIG. 2A.

FIGS. 2A and 2B, show a planar view and a side sectional view, respectively, of a paddle-style electrode platform 10 having an active surface 14, a back surface 17, a distal edge 11, a proximal edge 25, and side edge surfaces 8 and 9. A variety of electrode configurations or arrays are arranged and exposed on active surface 14. The side sectional view shown in FIG. 2B is taken along line 2B-2B shown in FIG. 2A. As shown in these figures, an exemplary electrode array 10 is shown in the form of a silicone paddle having a plurality of electrode contacts 12 arranged in two parallel rows on active surface 14 of the electrode array 10. The electrode contacts 12 are spaced apart from each other and each is electrically connected to a conductive wire(s) 15 that pass through or are embedded within the paddle portion 16 of the electrode 10.

The paddle electrode 10 is shown having two rows of eight contacts in parallel. A total of sixteen contacts are shown, but this is merely exemplary, and fewer or more contacts can be used. The electrode contacts 12 may be made, e.g., from platinum, platinum-iridium or similar materials known in the art for making electrode contacts.

The paddle-style electrode 10 may have more than one shape and the electrode contacts 12 may be in a variety of shapes and configurations. For example the paddle-style electrode 10 may have two or more columns of longitudinally staggered, rectangular-shaped electrode contacts 12. Arrays of circular-shaped electrode contacts and various other contact shapes are also possible. The electrode contacts 12 may vary in number and spacing, as well as shape and orientation.

Whichever type of electrode array is used, an important feature of the exemplary SCS system 100 shown in FIG. 1A is the ability to support the variety of electrode arrays available in the medical field, in conjunction with an insertion tool implementing a simple-to-use technique to localize the electrode array proximal to the stimulation site of a patient, as depicted in the description that follows.

Figure 3A:
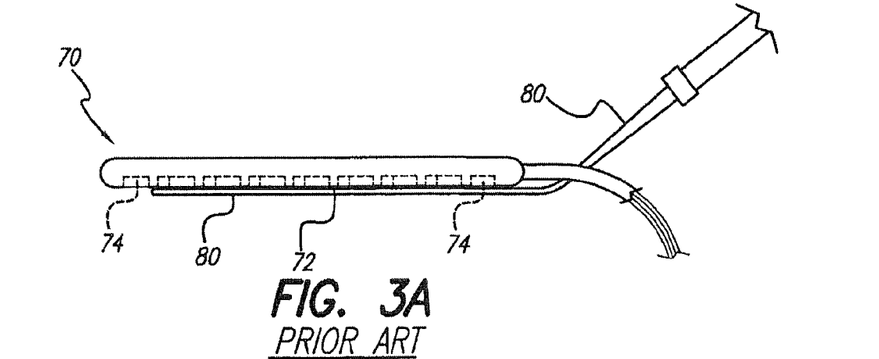
FIG. 3A is a side view showing an elevator tool and paddle-style electrode.
Figure 3B:
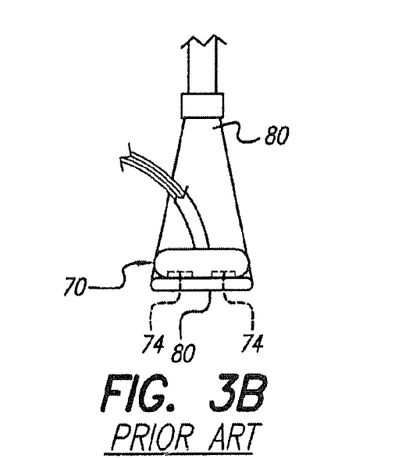
FIG. 3B is a front view of the embodiment shown in FIG. 3A.
Figure 3C:
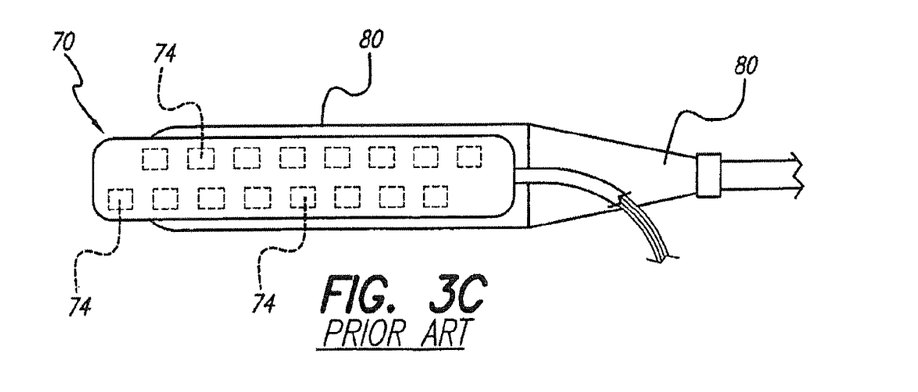
FIG. 3C is a top view of the embodiment shown in FIG. 3A.

Turning next to FIGS. 3A, 3B, and 3C, a conventional insertion technique is shown. FIG. 3A shows the side view of an elevator tool 80 and paddle-style electrode 70. FIGS. 3B and 3C, respectively, show a front view and a top view of the same insertion technique. The insertion technique represented in these figures is currently what surgeons are employing in conjunction with forceps to help them steer the electrode 70 to the stimulation site. Surgeons also use the elevator tool 80 to open the patient's epidural space 200 shown in FIG. 1B, followed by the use of the forceps to place the paddle-style electrode 70 in the localized stimulation site. The disadvantage in using this technique is the possibility of causing damage to the electrode 70 and/or electrode contacts 74 during the steering motion of the electrode 70, since surface 72 is in contact with the tool during insertion and implantation as shown in FIG. 3A.

Figure 4A:
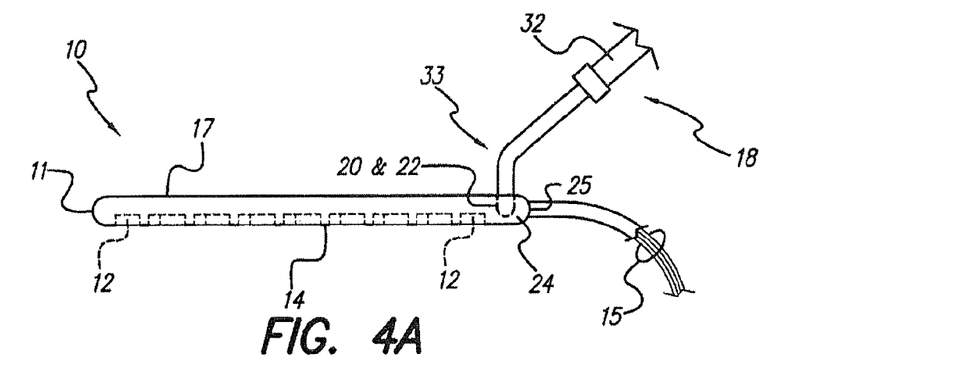
FIG. 4A is, in accordance with the present disclosure, a side view of an embodiment of the insertion tool having a "pin fork" (two pins) configuration holding a paddle-style electrode from the top surface wherein the electrode contacts face downward.

Referring now to FIG. 4A, in accordance with the present disclosure, a side view of one embodiment of an insertion tool 18 is shown. The insertion tool 18 is shown having a platform engager 33 with a "pin fork" construction, wherein two insertion pins or tines 28 and 30 are attached to the handle 32. The tool 18 can be engaged into a paddle-style electrode 10 from the back surface 17 through the holes 20 and 22 situated in the insulated region 24 of the paddle-style electrode 10, wherein the electrode contacts 12 are facing downward during implantation. Holes 20 and 22 may be constructed during the molding process of the paddle electrode 10 or they may be made after the molding process. Holes 20 and 22 should be situated in the insulated region 24 to avoid close placement to the area where the electrode contacts 12 are located. During the implant procedure, the insertion tool 18 with the "pin fork" construction can be used to positional adjust the paddle electrode in both the medial/lateral and inferior/superior directions giving the surgeon the ability to position and steer the paddle-style electrode 10 within the epidural space of the spinal column. Typically, forceps and elevator tool 80 as shown in FIGS. 3A, 3B, and 3C would be used by the surgeon, as these are among the few, if only, tools available to maneuver the paddle-style electrode 10 during surgery. Placement of the paddle electrode 10 is very critical and using an elevator tool 80 and forceps for steering the paddle electrode 10 can be problematic since the forceps and elevator tool can cause damage to the insulation and/or contacts 12 of the paddle-style electrode 10. The present "pin fork" configuration tool 18 shown in FIGS. 4A, 4B, and 4C offer a simpler technique for maneuvering the paddle-style electrode 10, without imparting damage to the contacts 12, wherein the contacts 12 are facing downward during implantation, as shown in FIG. 4A.

Figure 4B:
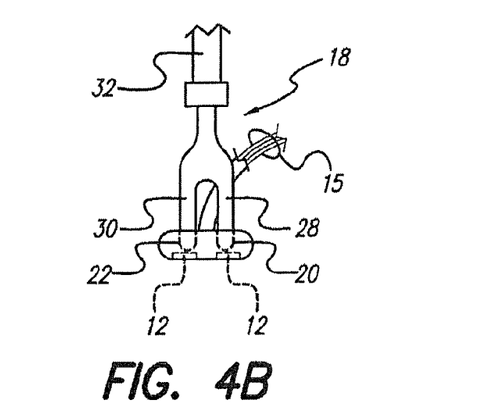
FIG. 4B is, in accordance with the present disclosure, a front view of the embodiment shown in FIG. 4A.
Figure 4C:
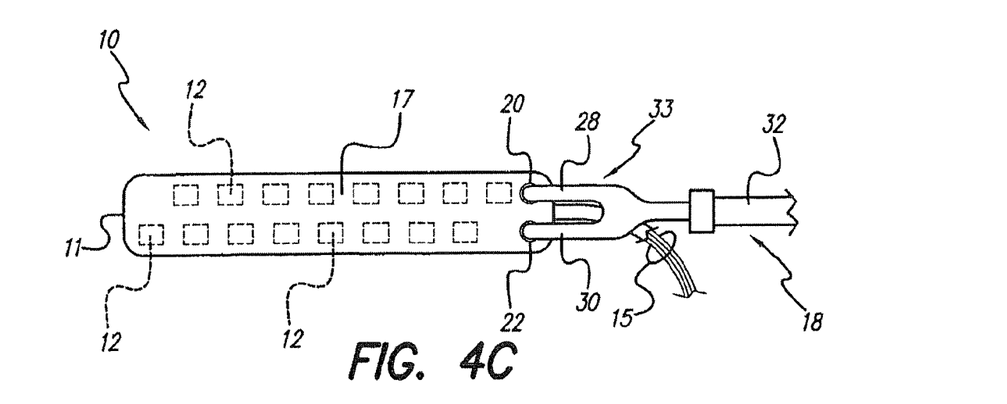
FIG. 4C is, in accordance with the present disclosure, a top view of the embodiment shown in FIG. 4A.
Figure 5A:
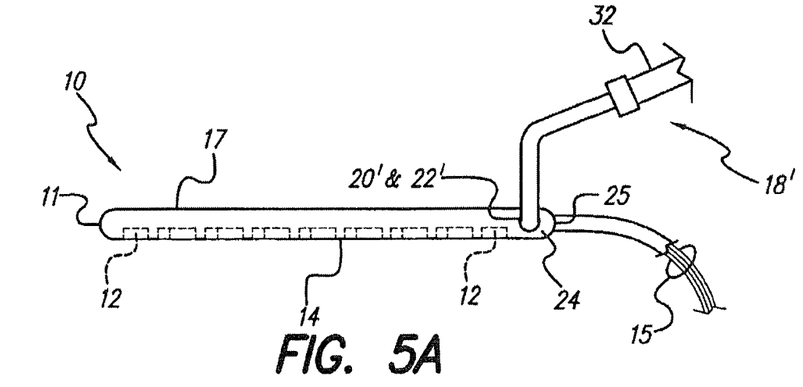
FIG. 5A is, in accordance with the present disclosure, a side view of an embodiment of the insertion tool having a "pin fork" (two pins) configuration holding a paddle-style electrode from the left and right surfaces wherein the electrode contacts face downward.
Figure 5B:
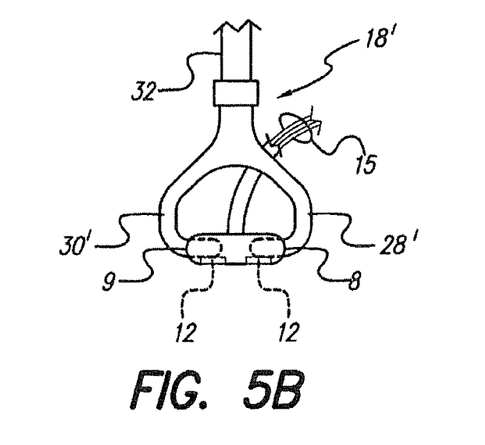
FIG. 5B is, in accordance with the present disclosure, a front view of the embodiment shown in FIG. 5A.
Figure 5C:
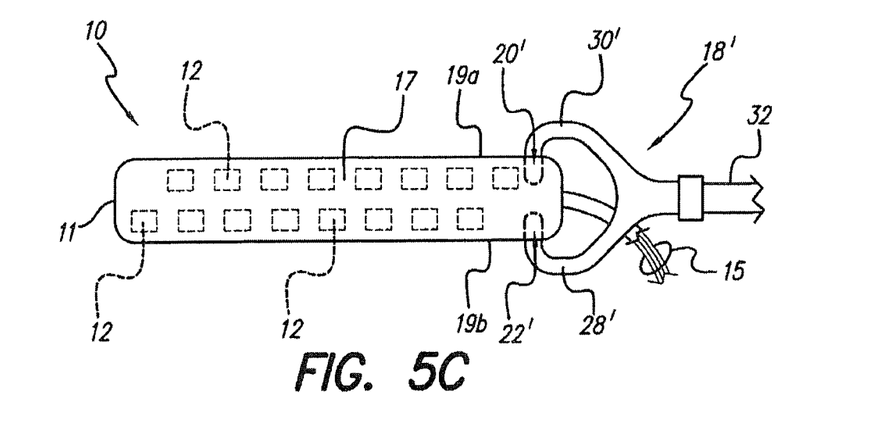
FIG. 5C is, in accordance with the present disclosure, a top view of the embodiment shown in FIG. 5A.

The "pin fork" design is represented by the two insertion pins or tines 28 and 30 as shown in FIGS. 4A, 4B, and 4C. The insertion pins 28 and 30 join together at the handle 32 of the "pin fork" insertion tool 18 and are engaged into the paddle-style electrode from the back surface 17. As an alternate embodiment of the present disclosure, the "pin fork" insertion tool 18 with insertion pins or tines 28 and 30 can be engaged through the bottom paddle active surface 14, wherein the electrode contacts 12 are facing downward during implantation. As another alternate embodiment shown in FIGS. 5A, 5B, and 5C, the fork pins 28' and 30' of the tool 18' can be inserted using side holes 20' and 22' situated in the side edge surfaces 8 and 9 of the paddle-style electrode 10, wherein the electrode contacts 12 are facing downward during implantation, as shown in FIG. 5A.

Figure 6A:
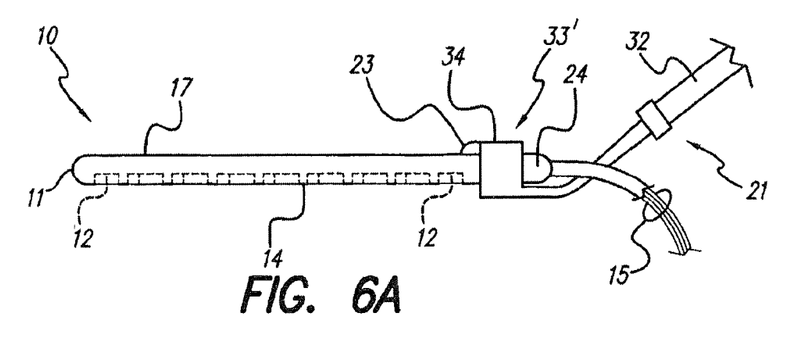
FIG. 6A is, in accordance with the present disclosure, a side view of another embodiment of the insertion tool together with the paddle-style electrode of the present invention wherein the electrode contacts face downward.
Figure 6B:
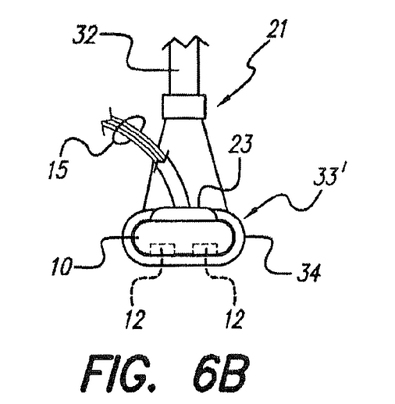
FIG. 6B is, in accordance with the present disclosure, a front view of the embodiment shown in FIG. 6A.
Figure 6C:
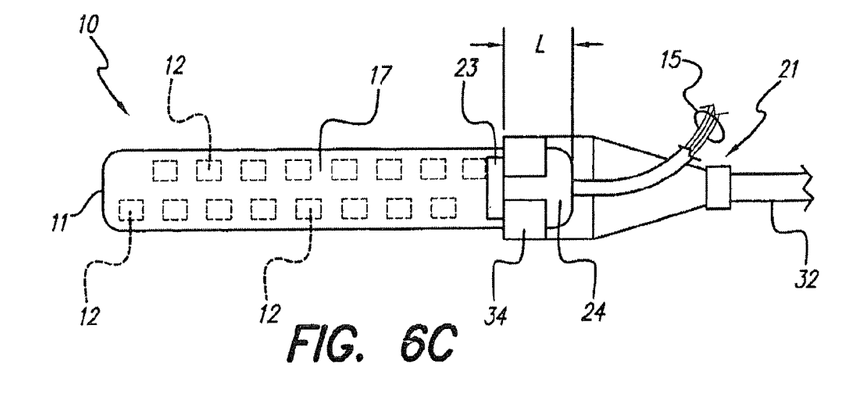
FIG. 6C is, in accordance with the present disclosure, a top view of the embodiment shown in FIG. 6A.

In the present disclosure, an insertion tool 21 having a "shovel" construction depicting another platform engager 33' is shown in FIGS. 6A, 6B, and 6C. FIG. 6A shows a side view of insertion tool 21 together with the paddle-style electrode 10. FIG. 6B shows a front view of insertion tool 21 and paddle-style electrode 10 and FIG. 6C shows a top view of insertion tool 21 and paddle-style electrode 10. The "shovel" configuration allows adjustment of the paddle-style electrode 10 in both the medial/lateral and inferior/superior directions within the epidural space 200 of the spinal column. As shown in FIG. 6C, a ridge or stopper 23, located a distance L from the proximal edge 25 of the electrode 10, may be made to hold the tool in place, allowing the necessary steering of the paddle-style electrode 10 during surgery. The carrier 34 of the tool holds the region 24 of the paddle electrode during the steering process avoiding damage to the contacts 12, wherein the electrode contacts 12 are facing downward during implantation as shown in FIG. 6A. The carrier 34 of the tool 21 can be alternatively configured to hold the paddle-style electrode 10 from the active surface 14 or the back surface 17, wherein the electrode 10 fits inside carrier 34. The carrier 34 is attached to a rod having a handle 32.

Figure 7A:
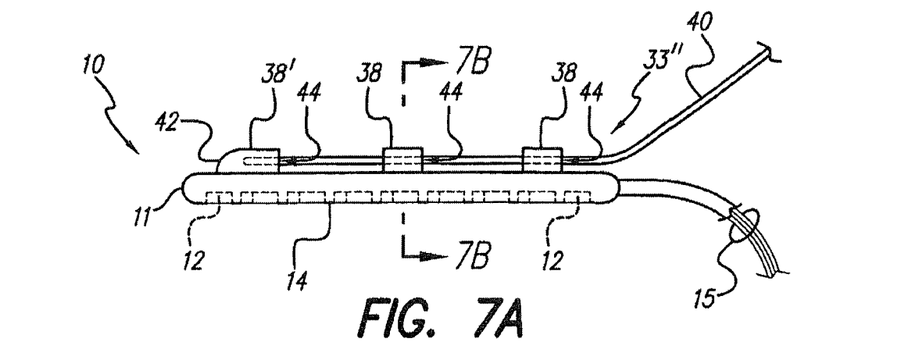
FIG. 7A is, in accordance with the present disclosure, a side view of another embodiment of an insertion technique using a stylet together with the paddle-style electrode wherein the electrode contacts face downward.
Figure 7B:
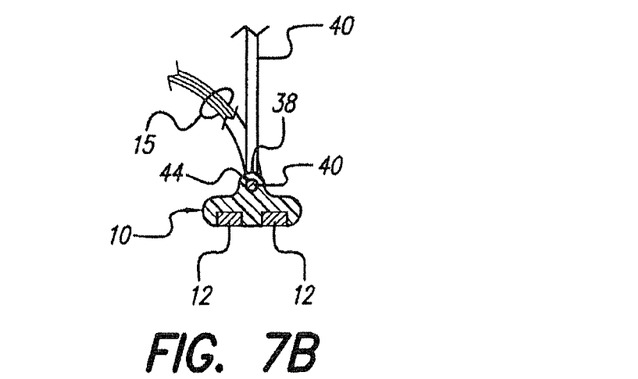
FIG. 7B is, in accordance with the present disclosure, a front sectional view of the embodiment shown in FIG. 7A taken along line 7B-7B.
Figure 7C:
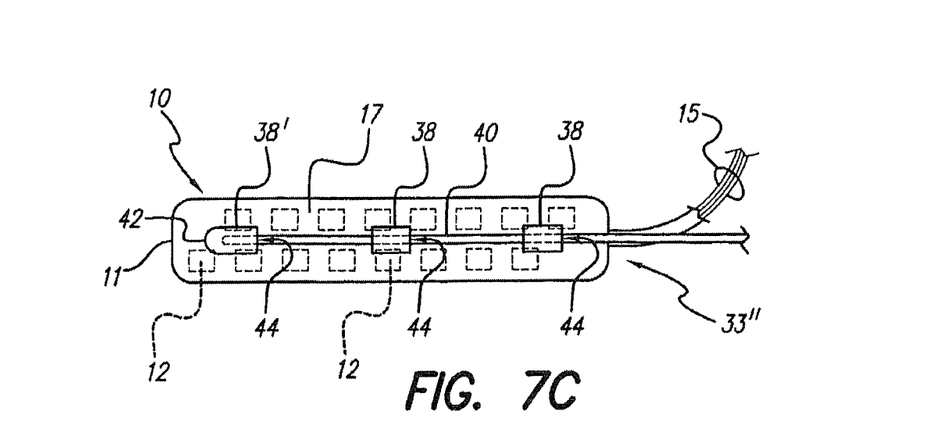
FIG. 7C is, in accordance with the present disclosure, a top view of the embodiment shown in FIG. 7A.

FIGS. 7A, 7B, and 7C, respectively show a side view, front sectional view, and top view of the present disclosure showing an insertion stylet 40 together with a paddle-style electrode 10, depicting yet another type of platform engager 33". FIGS. 7A, 7B, and 7C show a paddle electrode 10 with tabs 38, together with insertion stylet 40. The stylet 40 can be a flexible metal wire. As can be seen in these figures, there can be one or a series of projections or tabs 38 along the back surface 17 of the paddle-style electrode 10. The tabs 38 have holes 44 which allow access for the stylet 40 to be inserted. The end portion 42 of the final, end tab 38' is closed off or plugged to allow the stylet 40 to abut against the end of tab 38'. Once the stylet 40 is inserted through holes 44, maintaining the electrode contacts 12 facing downward as shown in FIG. 7A, the stylet 40 can be used to steer the paddle-style electrode 10 in both the medial/lateral and inferior/superior directions within the epidural space 200 of the spinal column and localize the paddle-style electrode 10 proximal the stimulation site, as shown in FIG. 1B.

FIG. 7C shows the top view of the insertion stylet 40 and paddle-style electrode 10. Two tabs 38 and one end tab 38' are shown. One or more projections or tabs 38 in conjunction with end tab 38' can be used to accommodate the insertion of the stylet 40. The end tab 38' is closed off at the tab end portion 42.

Figure 8A:
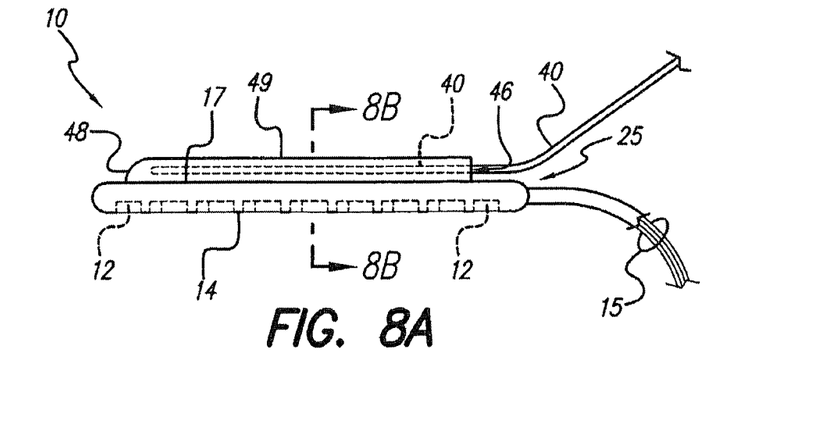
FIG. 8A is, in accordance with the present disclosure, a side view of another embodiment of an insertion technique using a stylet passing through a lumen together with the paddle-style electrode wherein the electrode contacts face downward.
Figure 8B:
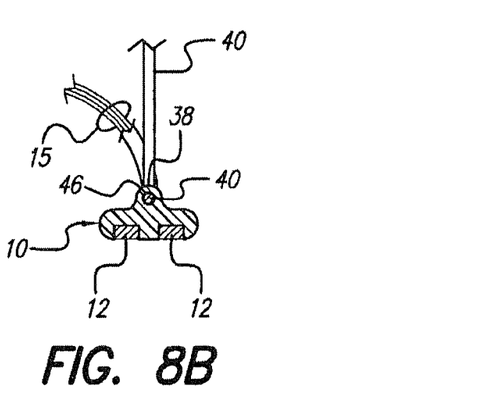
FIG. 8B is, in accordance with the present disclosure, a front sectional view of the embodiment shown in FIG. 8A taken along line 8B-8B.
Figure 8C:
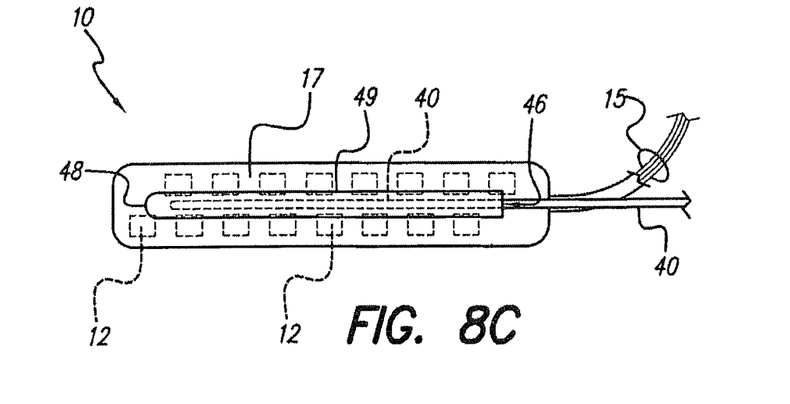
FIG. 8C is, in accordance with the present disclosure, a top view of the embodiment shown in FIG. 8A.

As an alternate embodiment shown in FIGS. 8A, 8B, and 8C, the paddle-style electrode 10 can have a longitudinal lumen 46, made through the projection or longitudinal ridge 49, to accommodate passage of the stylet 40. The distal end portion 48 of the lumen 46 is closed off or plugged to allow the insertion stylet 40 to abut against the insulated material. Once the stylet 40 is inserted through lumen 46, maintaining the electrode contacts 12 facing downward as shown in FIG. 8A, the stylet 40 can be used to steer the paddle-style electrode 10 in both the medial/lateral and inferior/superior directions within the epidural space 200 of the spinal column and localize the paddle-style electrode 10 proximity to the stimulation site. In yet a further embodiment, the stylet 40 using either the tabs 38 or lumen 46 can be maneuvered in conjunction with one of the implant tools 18, 18', or 21 described above.

Figure 9A:
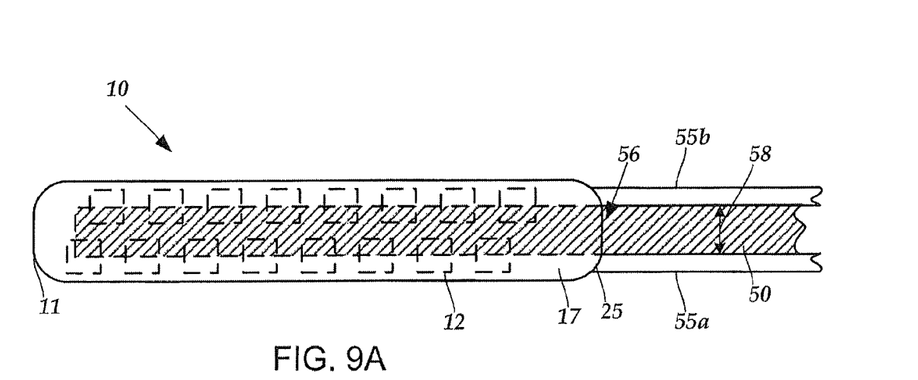
FIG. 9A is, in accordance with the present disclosure, a top view of another embodiment of an insertion technique using an insertion tool passing through a lumen together with the paddle-style electrode wherein the electrode contacts face downward.
Figure 9B:
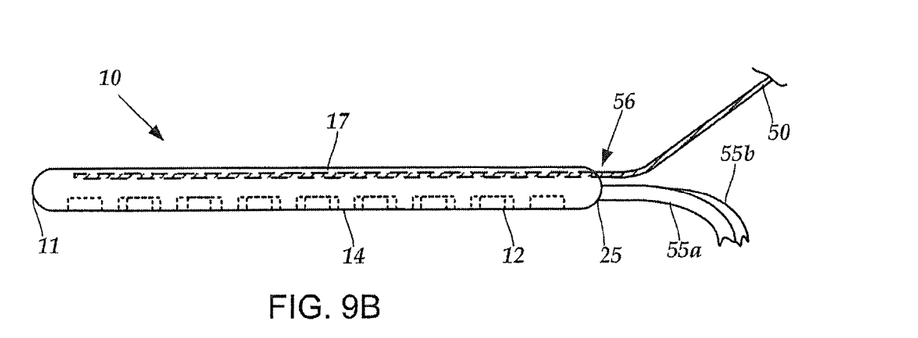
FIG. 9B is, in accordance with the present disclosure, a side view of the embodiment shown in FIG. 9A.

As another embodiment shown in FIGS. 9A and 9B, a lead includes a paddle-style electrode 10, with an array of electrode contacts disposed thereon, and one of more lead bodies 55a, 55b, containing the conductors 15 (see, FIGS. 2A-2B, 4A-8C), extending from the paddle-style electrode 10. The paddle-style electrode 10 has a longitudinal lumen 56, defined through the body of the paddle-style electrode (or alternatively through one or more projections disposed on the back surface of the paddle-style electrode similar to the projection(s) 38 illustrated in FIGS. 8A, 8B, and 8C), to accommodate insertion of a portion of an insertion tool 50 into the lumen. The illustrated insertion tool 50 has a flat body that is wider than the stylet 40 described above. In at least some embodiments, the insertion tool 50 has a lateral width (indicated by arrow 58) that is at least one-third or at least one-half the lateral width of the body of the paddle-style electrode 10.

The insertion tool 50, or at least the portion of the insertion tool 50 that is inserted into the lumen 56, is preferably made, or coated with, a low friction material, such as polytetrafluoroethylene (e.g., Teflon™), polycarbonate, polyetheretherketone (PEEK), or the like or combinations thereof. In at least some instances, the surface of the insertion tool 50, with the low friction material, has a coefficient of friction of 0.1 or less or in the range of 0.05 to 0.1. In at least some embodiments, the insertion tool 50 has a metal or plastic base covered with a layer or coating of the low friction material. It will be recognized that a low friction material can be used with other embodiments described herein. For example, a low friction material can be coated on, or used to make, the stylet 40 of FIGS. 7A-7C and 8A-8C or the insertion pins 28, 30, 28', 30' of FIGS. 4B, 4C, 5B, and 5C, described above, or at least the portion of the stylet or insertion pins that interacts with the paddle-style electrode 10.

Once the insertion tool 50 is inserted through lumen 56, the insertion tool 50 can be used to steer the paddle-style electrode 10 in both the medial/lateral and inferior/superior directions within, for example, the epidural space of the spinal column and localize the paddle-style electrode 10 in proximity to a desired stimulation site. The use of a low friction material for the insertion tool 50, or as a coating on the insertion tool 50, facilitates insertion of the insertion tool 50 into the lumen 56 and removal of the insertion tool 50 from the lumen 56 when the paddle-style electrode 10 is located at the stimulation site. This can reduce surgical time and reduce inadvertent displacement, due to friction between the paddle-style electrode 10 and insertion tool 50, of the paddle-style electrode 10 as the insertion tool 50 is removed. These considerations and techniques can also apply to a stylet 40 of FIGS. 7A-7C and 8A-8C or insertion pins 28, 30, 28', 30' of FIGS. 4B, 4C, 5B, and 5C that incorporate a low friction material.

Figure 10:
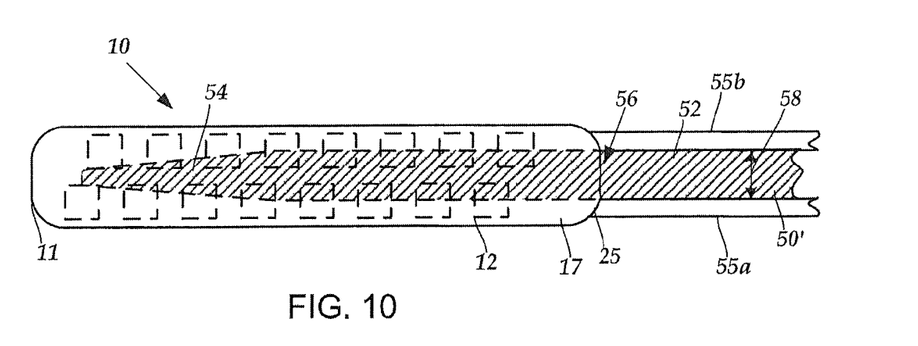
FIG. 10 is, in accordance with the present disclosure, a top view of another embodiment of an insertion technique using an insertion tool with a tapered distal section passing through a lumen together with the paddle-style electrode wherein the electrode contacts face downward.

As another embodiment shown in FIG. 10, an insertion tool 50' can have a distal tapered portion 54 and a straight portion 52, where at least part of the distal tapered portion 54 is inserted into the longitudinal lumen 56 of the paddle-style electrode 10 during implantation of the paddle-style electrode. The lateral width (identified by arrow 58 in FIG. 11) of the insertion tool 50' becomes narrower along the distal tapered portion 54, resulting in the tapering of this portion of the insertion tool. In at least some embodiments, the lateral width of the straight portion of the insertion tool is at least one-half or at least one-third of the lateral width of the paddle-style electrode and the lateral width at the distal end of the distal tapered portion of the insertion tool is no more than one-quarter, one-fifth, or one-sixth of the lateral width of the paddle-style electrode.

In at least some embodiments, as illustrated in FIG. 10, the entire distal tapered portion 54 and a part of the straight portion 52 are inserted into the longitudinal lumen 56 during implantation of the paddle-style electrode 10. In other embodiments, only part of the distal tapered portion of the insertion tool is inserted into the longitudinal lumen during implantation of the paddle-style electrode. Optionally, the insertion tool 50', or at least the portion of the insertion tool 50' that is inserted into the lumen 56, is preferably made, or coated with, a low friction material, such as polytetrafluoroethylene (e.g., Teflon™), polycarbonate, polyetheretherketone (PEEK), or the like or combinations thereof.

It is thought that reducing the area of contact between the insertion tool 50' and the paddle-style electrode 10 by tapering the distal portion of the insertion tool 50' will provide sufficient support during implantation of the paddle-style electrode, but reduce the surgical time for implantation and the amount of friction between the insertion tool and the paddle-style electrode.

Figure 11:
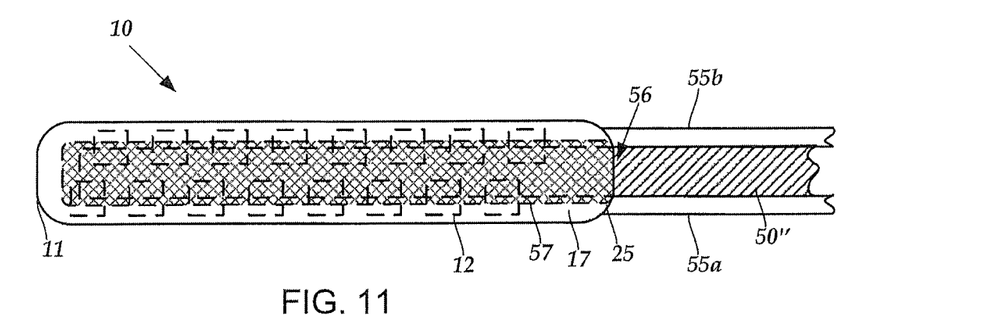
FIG. 11 is, in accordance with the present disclosure, a top view of another embodiment of an insertion technique using an insertion tool passing through a lumen together with the paddle-style electrode wherein the electrode contacts face downward.

As another embodiment shown in FIG. 11, the paddle-style electrode 10 can have a longitudinal lumen 56, made into the body of the paddle-style electrode (or alternatively into one or more projections disposed on the back surface of the paddle-style electrode similar to the projection(s) 38 illustrated in FIGS. 8A, 8B, and 8C but sufficiently wide) to accommodate passage of an insertion tool 50.

The interior surface of the lumen 56, or at least a portion of the interior surface of the lumen 56, is preferably coated with a low friction material, such as polytetrafluoroethylene (e.g., Teflon™), polycarbonate, polyetheretherketone (PEEK), or the like or combinations thereof. In at least some instances, the interior surface of the lumen 56, with the low friction material, has a coefficient of friction of 0.1 or less or in the range of 0.05 to 0.1. In some embodiments, at least a portion of the insertion tool may also contain a low friction material is described above with respect to the embodiment illustrated in FIGS. 9A and 9B. It will be understood that application of the low friction material to a portion of the paddle-style electrode that interacts with an insertion tool can also be used with other embodiments described herein. For example, a low friction material can be coated within the holes 20, 22, 20', 22' of FIGS. 4B, 4C, and 5A-5C or within the holes 44 in the tabs 38, 38' of FIGS. 7A-7C or in the longitudinal lumen 46 of the ridge 49 of FIGS. 8A-8C, described above.

Although the insertion tools 50, 50' described above have been illustrated with a rectangular cross-sectional shapes, it will be understood that insertion tools with triangular, oval, elliptical, circular, or other cross-sectional shapes can be used. In some embodiments, different portions of the insertion tool 50, 50' can have different cross-sectional shapes, or different diameters, widths, or thicknesses. Differences embodiments in the cross-sectional shape of embodiments of the insertion tool 50, 50', and the shape of the longitudinal lumen 56 in the paddle-style electrode 10, can provide different steerability, insertion, and removal characteristics.

Those skilled in the art will recognize various other insertion methods of retaining a paddle-type electrode with the platform engagers depicted by the various tools described in the present disclosure and others available in the surgical field. Those other methods are intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A system for lead implantation, comprising
  a lead comprising
    a paddle-style electrode extending from a proximal end to a distal end, the paddle-style electrode, comprising a back surface; an active surface; a plurality of electrode contacts disposed on the active surface; and a longitudinal lumen extending into the paddle-style electrode and defining an opening at the proximal end of the paddle-style electrode, and
    at least one lead body extending from the paddle-style electrode, the at least one lead body comprising a plurality of conductors that are electrically coupled to the plurality of electrode contacts; and
  an insertion tool having a distal portion configured and arranged for insertion of the distal portion of the insertion tool into the longitudinal lumen of the paddle-style electrode, wherein the distal portion of the insertion tool is tapered to narrow a lateral width of the insertion tool along the distal portion, wherein a lateral width of the insertion tool at a proximal end of the distal portion of the insertion tool is at least one half of a lateral width of the paddle-style electrode and a lateral width of the insertion tool at a distal end of the distal portion of the insertion tool is no more than one quarter of a lateral width of the paddle-style electrode.

2. The system of claim 1, wherein the lateral width of the insertion tool at the distal end of the distal portion of the insertion tool is no more than one fifth of the lateral width of the paddle-style electrode.

3. The system of claim 1, wherein the lateral width of the insertion tool at the distal end of the distal portion of the insertion tool is no more than one sixth of the lateral width of the paddle-style electrode.

4. The system of claim 1, wherein the insertion tool further comprises a straight portion extending proximally from the distal portion.

5. The system of claim 4, wherein a lateral width of the straight portion of the insertion tool is at least one half of a lateral width of die paddle-style electrode.

6. The system of claim 4, wherein the longitudinal lumen of the paddle-style electrode is configured and arranged to receive all of the tapered portion of the insertion tool and a part of the straight portion of the insertion tool.

7. The system of claim 1, wherein at least the distal portion of the insertion tool comprises a low friction material forming a surface of the distal portion of the insertion tool with a coefficient of friction of 0.1 or less.

8. The system of claim 1, wherein the longitudinal lumen comprises an interior surface with a coating of low friction material disposed on the interior surface to provide the interior surface with a coefficient of friction of 0.1 or less.

9. A method of using the system of claim 1, the method comprising:
  inserting at least a part of the distal portion of the insertion tool into the longitudinal lumen of the paddle-style electrode of the lead; and
  implanting the paddle-style electrode into patient tissue using the insertion tool to guide implantation.

10. The method of claim 9, wherein the insertion tool further comprises a straight portion extending proximally from the distal portion and wherein inserting at least a part of the distal portion of the insertion tool comprises inserting all of the tapered portion of the insertion tool and a part of the straight portion of the insertion tool into the longitudinal lumen of the paddle-style electrode.

11. The method of claim 9, wherein the insertion tool further comprises a straight portion extending proximally from the distal portion and wherein inserting at least a part of the distal portion of the insertion tool comprises inserting less than all of the tapered portion of the insertion tool into the longitudinal lumen of the paddle-style electrode.

12. A system for lead implantation, comprising
  a lead comprising
    a paddle-style electrode extending from a proximal end to a distal end, the paddle-style electrode, comprising a back surface; an active surface; a plurality of electrode contacts disposed on the active surface; and a longitudinal lumen extending into the paddle-style electrode and defining an opening at the proximal end of the paddle-style electrode, and
    at least one lead body extending from the paddle-style electrode, the at least one lead body comprising a plurality of conductors that are electrically coupled to the plurality of electrode contacts; and
  an insertion tool having a distal portion configured and arranged for insertion of the distal portion of the insertion tool into the longitudinal lumen of the paddle-style electrode, wherein the distal portion of the insertion tool is tapered to narrow a lateral width of the insertion tool along the distal portion, wherein a lateral width of the insertion tool at a proximal end of the distal portion of the insertion tool is at least one third of a lateral width of the paddle-style electrode and a lateral width of the insertion tool at a distal end of the distal portion of the insertion tool is no more than one quarter of a lateral width of the paddle-style electrode.

13. The system of claim 12, wherein the lateral width of the insertion tool at the distal end of the distal portion of the insertion tool is no more than one fifth of the lateral width of the paddle-style electrode.

14. The system of claim 12, wherein the lateral width of the insertion tool at the distal end of the distal portion of the insertion tool is no more than one sixth of the lateral width of the paddle-style electrode.

15. The system of claim 12, wherein the insertion tool further comprises a straight portion extending proximally from the distal portion.

16. The system of claim 15, wherein a lateral width of the straight portion of the insertion tool is at least one third of a lateral width of the paddle-style electrode.

17. The system of claim 15, wherein the longitudinal lumen of the paddle-style electrode is configured and arranged to receive all of the tapered portion of the insertion tool and a part of the straight portion of the insertion tool.

18. A method of using the system of claim 12, the method comprising:
   inserting at least a part of the distal portion of the insertion tool into the longitudinal lumen of the paddle-style electrode of the lead; and
   implanting the paddle-style electrode into patient tissue using the insertion tool to guide implantation.

19. The method of claim 18, wherein the insertion tool further comprises a straight portion extending proximally from the distal portion and wherein inserting at least a part of the distal portion of the insertion tool comprises inserting all of the tapered portion of the insertion tool and a part of the straight portion of the insertion tool into the longitudinal lumen of the paddle-style electrode.

20. The method of claim 18, wherein the insertion tool further comprises a straight portion extending proximally from the distal portion and wherein inserting at least a part of the distal portion of the insertion tool comprises inserting less than all of the tapered portion of the insertion tool into the longitudinal lumen of the paddle-style electrode.

\* \* \* \* \*